United States Patent [19]
Hampp et al.

[11] Patent Number: 5,783,056
[45] Date of Patent: Jul. 21, 1998

[54] ELECTROCHEMICAL ENZYME BIOSENSOR

[75] Inventors: Norbert Hampp, München; Anton Silber, Mering; Christoph Bräuchle, München, all of Germany

[73] Assignee: Bayer Corporation, Pittsburgh, Pa.

[21] Appl. No.: 560,939

[22] Filed: Nov. 20, 1995

[30] Foreign Application Priority Data

Nov. 28, 1994 [DE] Germany .................. 44 42 253.9

[51] Int. Cl.$^6$ .................................................. G01N 27/26
[52] U.S. Cl. .................. 204/403; 204/415; 435/287.1; 435/289.1; 435/817
[58] Field of Search ............................ 204/403, 415, 204/418; 435/288, 291, 817

[56] References Cited

U.S. PATENT DOCUMENTS

| | | | |
|---|---|---|---|
| 5,122,456 | 6/1992 | Bennetto et al. | 435/76 |
| 5,217,594 | 6/1993 | Henkens et al. | 204/403 |
| 5,240,571 | 8/1993 | Heineman et al. | 204/153 |
| 5,468,366 | 11/1995 | Wegner et al. | 204/403 |
| 5,540,828 | 7/1996 | Yacynych | 204/403 |

FOREIGN PATENT DOCUMENTS 4027728   3/1992   Germany .

OTHER PUBLICATIONS

Wang et al, Anal. Chem. 1994, 66, 1007–1011 "Enzyme Microelectrode Array Strips for GLucose and Lactate", no month available.

Blaedel et al, Analytical Chemistry, vol. 47, No. 8, Jul. 1975 "Study of the Electrochemical Oxidation of Reduced Nicotinamide Adenine Dinucleotide".

Schmidt et al, Fresenius J. Anal. Chem. (1994) 349:607–612 "Application of Screen Printed Electrodes in Biochemical Analysis", no month available.

Gorton et al, Analytica Acta, 249 (1991) 43–54 "Amperometric Glucose Sensors Based on Immobilized Glucose-Oxidizing Enzymes and Chemically Modified Electrodes", no month available.

Gorton, L. J. Chem. Soc., Faraday Trans. I, 1986, 82, 1245–1258 "Chemically Modified Electrodes for the Electrocatalytic Oxidation of Nicotinamide Coenzymes", no month available.

*Primary Examiner*—Bruce F. Bell
*Attorney, Agent, or Firm*—Jerome L. Jeffers

[57] ABSTRACT

In the case of the electrochemical enzyme biosensor comprising noble metal electrodes, an electrochemical oxidation of pyridine nucleotides takes place, in particular of NADH. The noble metal electrodes have a microtexture rich in surface pores and having catalytic properties, as a result of which the overpotential required for electrochemical oxidation of the pyridine nucleotides is reduced. Owing to these microtextures, the surface area of an electrode is from 3 to 10 times larger than its geometric surface area.

9 Claims, 4 Drawing Sheets

ELECTROCHEMICAL ENZYME BIOSENSOR

The invention is based on an electrochemical enzyme biosensor which comprises noble metal electrodes and with which an electrochemical oxidation of pyridine nucleotides, in particular of NADH takes place.

BACKGROUND OF THE INVENTION

Numerous enzyme analysis methods in clinical diagnostics and in environmental, process and food analysis are based on reactions which are catalyzed by enzymes of the dehydrogenase class. This involves utilizing the direct proportionality between the concentration of the substrate to be analyzed on the one hand and the concentration of the coenzyme NADH formed or consumed on the other hand. Most of these methods take advantage of optical properties of the molecule NADH, which differs, for example, from its corresponding oxidized form $NAD^+$ by a characteristic absorption of light having a wavelength of 360 nm. In the case of coloured or turbid analytes, these spectrophotometric methods will largely fail or at least require a laborious and time-consuming pretreatment of the samples. This can be circumvented by electrochemical detection of NADH. Moreover, direct, stable coupling of electrodes and enzyme to form electrochemical biosensors is possible. The drawback of the electrochemical method has hitherto been the high overpotential required for oxidizing NADH. This also results in the detection of a number of further substances which are likewise present in the analyte, so that unduly high analysis values are normally obtained, which subsequently have to be corrected. Moreover the electrochemical oxidation of NADH at high overpotentials leads, via radical intermediates, to dimers and oligomers of NADH which permanently coat the electrode surface and cause lasting damage (so-called electrode fouling, cf. W. J. Blaedel & R. A. Jenkins, Study of the electrochemical oxidation of reduced nicotinamide adenine dinucleotide. Anal. Chem. 47 (1975) 1337–1343). To circumvent this phenomenon, the analyte is often admixed with catalytic amounts of low-molecular weight molecules which are able to undergo redox reactions and which effect the transport of the electrons from NADH to the electrode (cf., amongst many others, L. Gorton, Chemically modified electrodes for the electrocatalytic oxidation of nicotinamide coenzymes, J. Chem. Soc. Faraday Trans. 82 (1986) 1245–1258). These so-called mediators are in part immobilized on the electrode, although in view of the restriction of the mediator having to remain mobile in order to be effective, stable binding of the mediator to the electrode is often not possible. The mediator diffuses into the analyte, to the considerable detriment of the stability of the sensors.

A method described in U.S. Pat. No. 5,240,571 employs a coupling reagent capable of undergoing redox reactions, which is added to the analyte and, with NADH, forms an electroactive compound which is oxidized at low overpotentials. U.S. Pat. No. 5,122,457 discloses that NADH can be oxidized quantitatively on porous carbon electrodes and graphite electrodes coated with platinum or palladium, the potential employed not being specified.

The object of the invention is to improve an electrochemical enzyme biosensor comprising noble metal electrodes in such a way, without adding a mediator to the analyte and without any chemical modification of the electrode, that any interfering substances which may be present in the analyte and which are likewise electrochemically oxidizable are largely unable to enter into any electrode reaction. In addition to the higher selectivity thus obtained, the stability of the transductor electrodes and thus the operational stability of the sensors fabricated therefrom is to be enhanced.

SUMMARY OF THE INVENTION

This object is achieved, according to the invention, and starting from an electrochemical enzyme biosensor which comprises noble metal electrodes and with which an electrochemical oxidation of pyridine nucleotides takes place, by the noble metal electrodes having a microtexture rich in surface pores and having catalytic properties, as a result of which the overpotential required for electrochemical oxidation of the pyridine nucleotides is reduced. The microtexture rich in surface pores is caused by numerous microscopically small peaks and craters, so that the surface area of the electrodes is considerably increased. The peaks consist of noble metal particles or of particle clusters which project from the electrode surface and have a mean radius of curvature of from 0.05 μm to 4 μm, preferably from 0.5 μm to 2 μm. This microroughness increases the surface area of an electrode by approximately a factor of from 3 to 10, preferably from 4 to 7 (compared with the geometric surface area), which can be demonstrated by electron microscopy and impedance spectroscopy measurements.

This special microtexture, rich in surface pores, of the noble metal electrodes results in the electrodes having catalytic properties which manifest themselves in a drastic reduction of the overpotential for the oxidation of pyridine nucleotides, especially of NADH. It was found that the overpotential required for the anodic oxidation of NADH to $NAD^+$ is reduced to from 0 to 200 mV, preferably to from 100 to 150 mV, against the SCE and is thus at least 50% below the values normally found.

Particularly good results are achieved if the microporous noble metal electrodes are made of gold.

Immobilization of the selectivity-determining enzymes can preferably be effected by a membrane containing the enzyme being applied to the working electrode. Adhesion of the membrane on the planar electrode is promoted by the above-described microroughness of the electrode. The use, in particular, of membranes made from an aqueous poly (vinylacetate) dispersion, such as are described, e.g., in German Patent Specification 40 27 728, allows stable, selective, highly sensitive biosensors to be obtained.

According to a further development, the microporous noble metal electrodes are modified by coating them with electropolymerizable, conductive polymers, in particular with polypyrrole and poly(methylene blue). This modification can be utilized for the immobilization of enzymes and other selectivity-conferring biocomponents. In the process, the disperse surface of the noble metal electrodes enables homogeneous growth of the polymer during the electropolymerization, since many reactive sites, uniformly distributed over the entire macroscopic electrode surface, are generated.

If the electrochemical polymerization is carried out in the presence of an enzyme, this is immobilized by being physically trapped in the polymer during the growth of the latter in front of the electrode. The polymer skeleton firstly serves to immobilize the enzyme, but also has the function of a sieve which prevents large molecules, e.g. proteins, from reaching the electrode surface, coating it and thus at least reversibly damaging it. Furthermore, the polymer, if it has redox sites, can act as a catalytic mediator for the electron transfer from the enzyme or the coenzyme to the metal electrode. In the case of poly(methylene blue), the amplitude of the amperometric signal can therefore be distinctly increased (factor 10), which has a beneficial effect on the signal-to-noise ratio and thus results in a lower detection limit and an enhanced sensitivity for the substances to be determined.

Alternatively, enzymes or other biocomponents are immobilized directly on the electrodes via reactive pendent groups. This permits the construction of biosensors having extremely short response times, compared with membrane biosensors, since the component to be measured does not have to diffuse through a membrane. Some enzymes such as, e.g., glucose oxidase, are glycoproteins whose polysaccharide envelope is suitable for chemical linking to bifunctional spacer molecules. These spacers are bound to the sugar residues of the glycoprotein via one of their two functional groups, e.g. by an amino function, whereas the other functional terminal group, e.g. a thiol group, enters into a stable bond with the surface of the gold electrodes. In the case of glucose oxidase, the enzyme lyophilisate is dissolved in a carbonate buffer (pH 8.1) and after the addition of one per cent strength ethanolic 2,4-dinitrofluorobenzene solution, is admixed with sodium periodate solution (60 mM), whereupon a so-called periodate cleavage of the sugar component of the enzyme takes place. Reactive carbonyl groups generated in the process are then, after a dialytic purification step, coupled with a bifunctional thio, e.g. with cystamine, via its amino groups. The modified enzyme obtained is stably bound to the gold surface via the thiol groups of the cystamine radical.

The above-described microtextures rich in surface pores are produced, in the course of the fabrication of gold electrodes, by a chemically inert base being coated, by means of screen printing, with a paste comprising a gold powder and a polymeric binder, and the coated base then being passed through a furnace having incrementally gradated firing temperature zones, the temperature of the first firing zone being from 300° C. to 400° C. and that of the last firing zone being from 800° C. to 950° C. The residence time of the coated base in this process is preferably approximately 3 min to 8 min.

The invention provides the following advantages:

It was found that the overpotential for the anodic oxidation of NADH to $NAD^+$ on the noble metal electrodes fabricated by a thick-film technique by means of screen printing is reduced to such an extent that—in contrast to conventional noble metal electrodes, which require an overpotential of +600 mV—for the purpose of amperometric measurements of NADH concentrations, overpotentials of less than +200 mV against a KCl-saturated aqueous calomel reference electrode (SCE) will suffice. The reduction in the overpotential results in any interfering substances cooxidizable at high overpotentials, which may be present in the liquid analyte, no longer undergoing electrochemical reactions and no longer falsifying the result of the analysis. The noble metal electrodes described are utilized especially as transductors for electrochemical enzyme biosensors based on dehydrogenases. The main fields of application of these sensors are clinical diagnostics and environmental, process and food analysis.

The invention is explained below in more detail with reference to a fabrication example and to illustrative measurements.

Fabrication Example

A gold powder having a mean particle size of 1.5 μm and a size distribution of from 1 μm to 3.5 μm is intimately mixed with a nitrocellulose-containing polymeric binder.

The gold paste thus prepared is then applied by screen-printing to a ceramic base plate having the dimensions $41 \times 41 \times 0.5$ $mm^3$. Then the coated base plate is run, at a speed of 8 cm/min, through a furnace comprising six firing zones, each 60 cm in length, having the following temperature profile:

| | |
|---|---|
| 1st zone | 336° C. |
| 2nd zone | 685° C. |
| 3rd zone | 872° C. |
| 4th zone | 905° C. |
| 5th zone | 857° C. |

The particle size distribution of the gold particles in the screen printing paste employed and their radii determine the subsequent surface properties and the porosity of the gold electrodes. Additionally, minute explosions which take place during the pyrolysis of the polymer fraction result in sharp-edged craters forming on the gold surface which likewise affect the surface properties. The minute explosions are caused by polymer layers situated further down being pyrolyzed so rapidly that the gas diffusion of the layers lying above them is not sufficient to bring down the resulting pressure. By means of comparative impedance spectroscopy measurements of the actual surface area of conventional, polished gold electrodes and of gold electrodes prepared by a thick-film technique it was shown that the latter, given an identical geometric surface area, have six times as large an actual surface area.

BRIEF DESCRIPTION OF THE DRAWINGS

Illustrative measurements according to FIGS. 1 to 4.

In the figures.

DETAILED DESCRIPTION OF THE PREFERRED EMBODIMENTS

Figure 1:
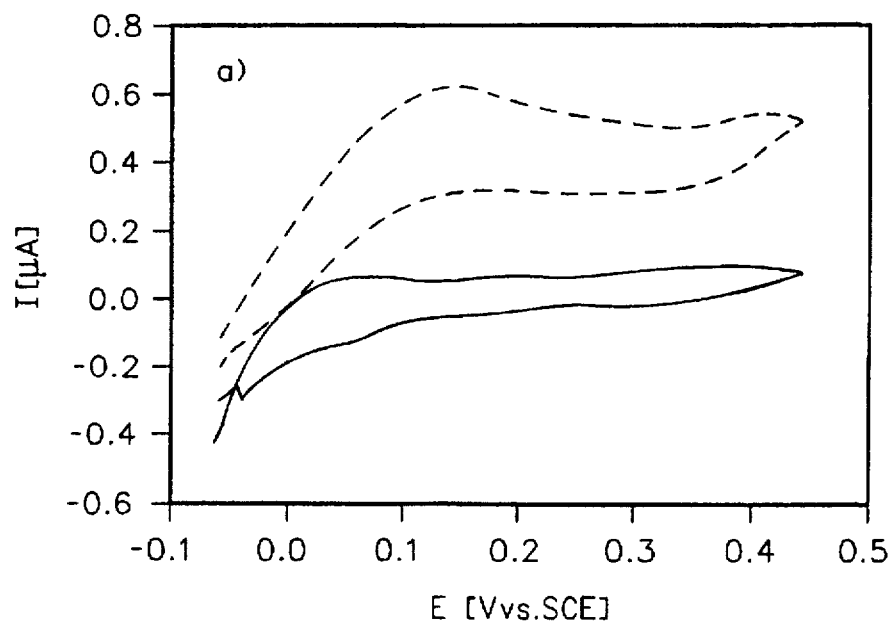
FIGS. 1 and 1a shows the cyclic voltammograms of (a) a microporous thick-film gold electrode and (b) a commercially available planar gold electrode polished to mirror brightness (EG & G) in buffered solutions with ( . . . ) and without (—) the addition of NADH.
Figure 1A:
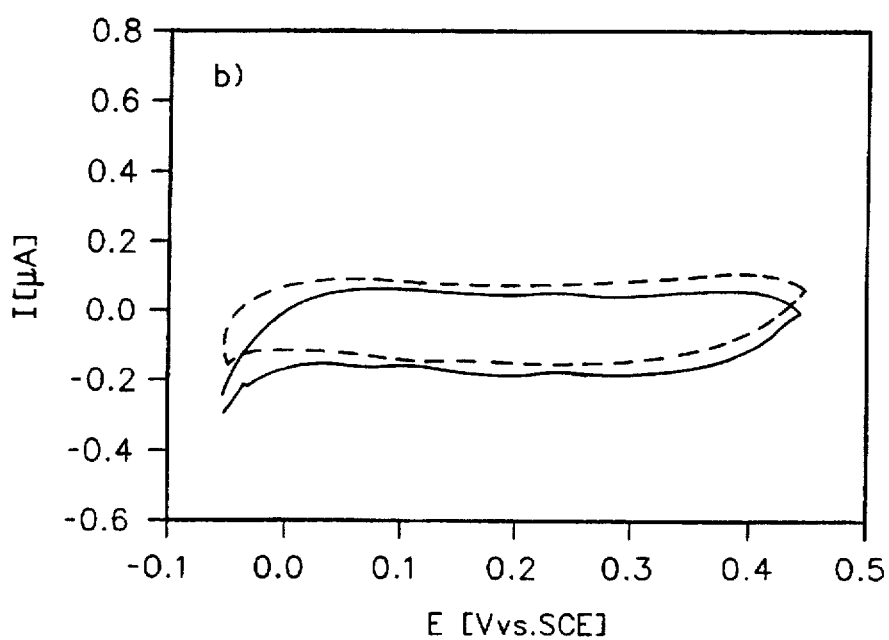

FIG. 1 illustrates the catalytic activity of the electrodes according to the invention with respect to the anodic oxidation of NADH. In the course of the cyclic voltammogram there appears, in the case of the thick-film gold electrode (a) in the presence of NADH (1), starting at approximately +100 mV (against SCE), a distinct anodic current which is caused by the oxidation of NADH. With the NADH-free buffer (2) this current is absent. With conventional electrodes (b), such behaviour cannot be observed under identical experimental conditions (3, 4). The cyclic voltammograms were recorded in 0.1M sodium phosphate buffer of pH 7.0, which contained 0.1M sodium perchlorate as the supporting electrolyte. The voltage rate was 10 mV/sec. The NADH concentration was 0 mM (2, 4) and 5 mM (1, 3), respectively.

Figure 2:
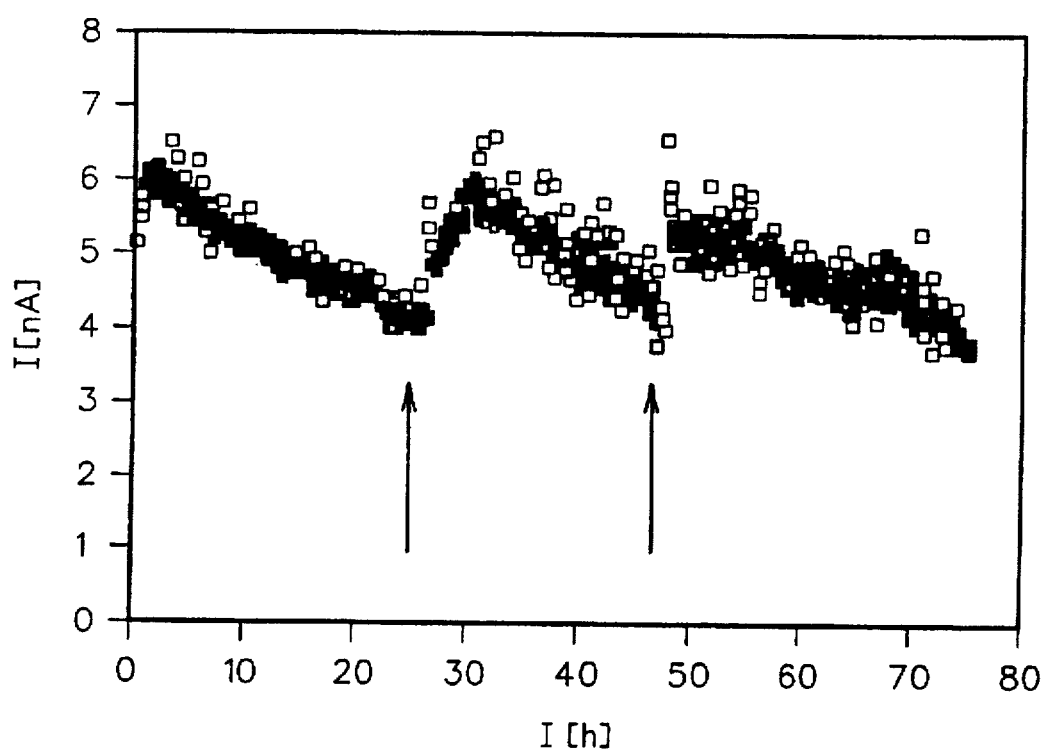
FIG. 2 shows the long-term stability of a microporous gold electrode during the measurement of NADH.

The thick-film gold electrodes according to the invention were incorporated into a flow injection system for detecting 0.5 mM NADH and were operated at +145 mV (against SCE). FIG. 2 shows the change of the anodic current against time for the oxidation of NADH. The arrows indicate that in each case freshly prepared NADH solutions were used. The drop in the current after the introduction of a fresh solution therefore mainly results from the thermal decomposition of NADH in solution (0.1M sodium phosphate buffer, pH 7.0 with 0.1M sodium perchlorate, room temperature) and is not due, or only to a limited extent, to electrode fouling.

Figure 3:
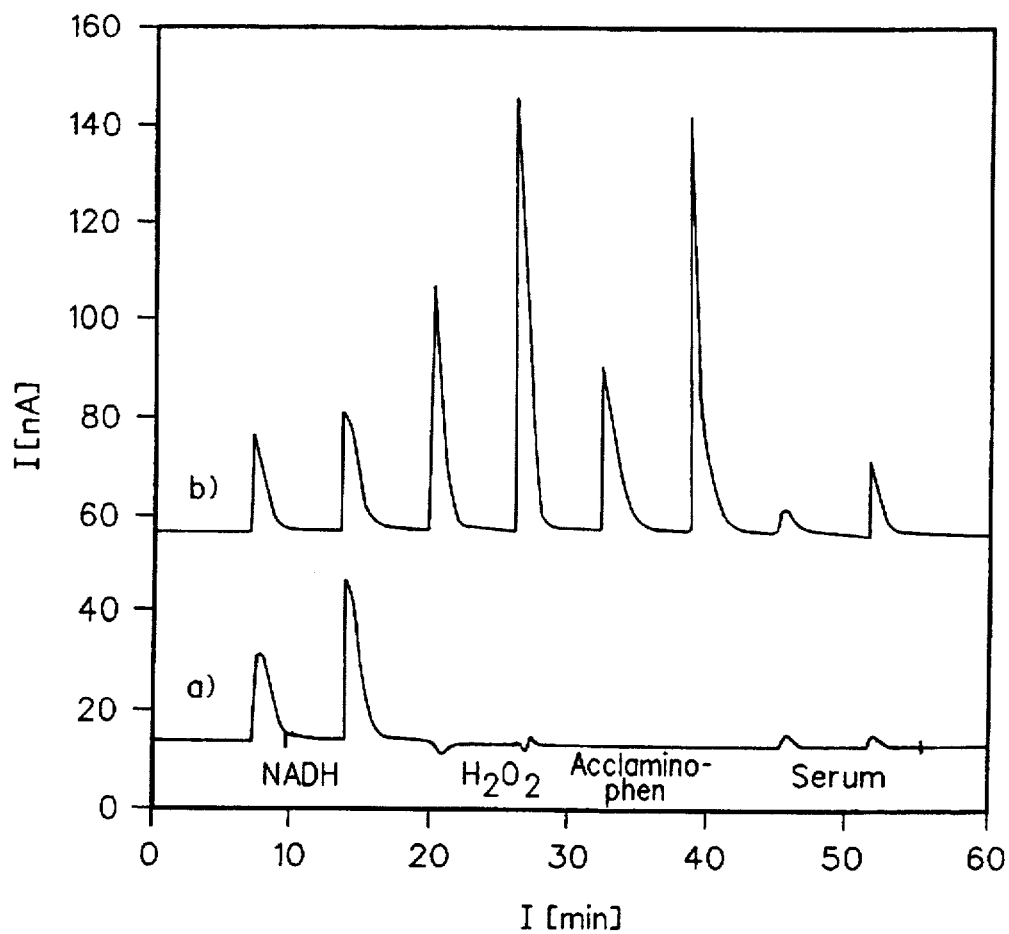
FIG. 3 shows the effect of interfering substances in the case of conventional potentials and potentials made possible by the invention, for the oxidation of NADH.

To clarify the advantages of sensor operation at low polarization voltages, potentially interfering substances (1 and 2 mM hydrogen peroxide, 1 and 2 mM acetaminophen (=paracetamol), serum diluted 1:1 and undiluted) were studied together with NADH (1 and 2 mM) in a flow injection system (FIG. 3). In so doing, in one case, the voltage most common hitherto of (a) +555 mV was applied to the electrodes and (b) in another case at the lower potential of +145 mv (both against SCE), which is sufficient to oxidize NADH, using the electrodes according to the invention. Apart from NADH, nothing was indicated at this low potential except, to a small extent, serum components.

Figure 4:
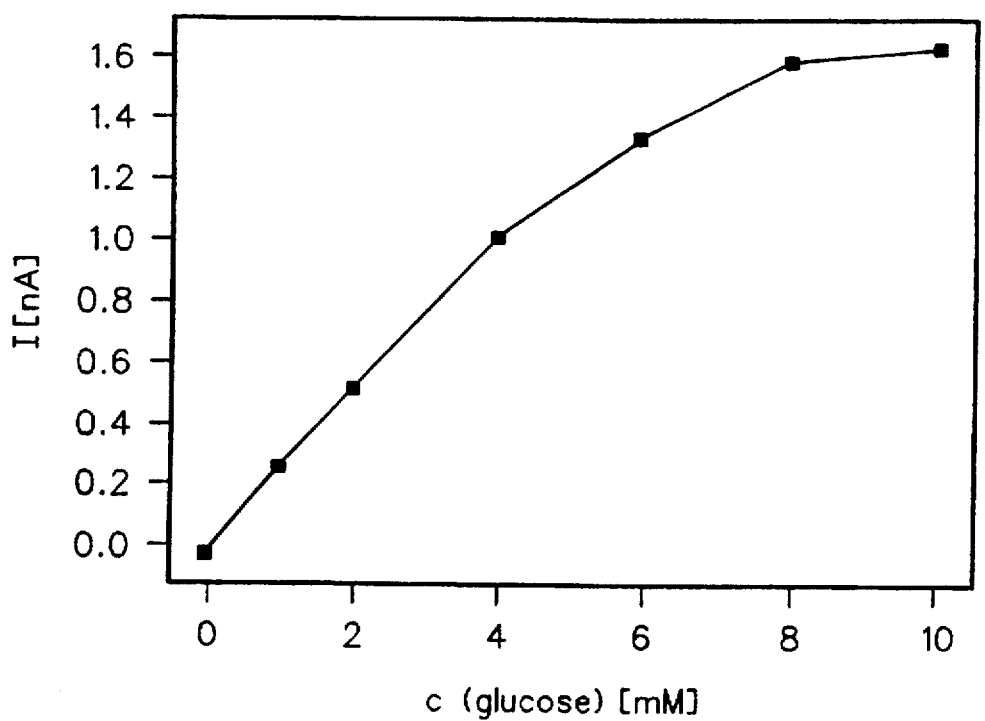
FIG. 4 shows the concentration-current characteristic of a glucose biosensor which, employing the electrode according to the invention as a transductor, operates at low polarization voltages.

The glucose biosensor whose calibration curve is reproduced in FIG. 4 represents a possible application for the electrodes according to the invention. The enzyme glucose dehydrogenase was immobilized onto the gold surface by matrix inclusion into a poly(vinyl acetate) membrane. The calibration curve was recorded in a flow injection system which was operated with 0.1M sodium phosphate buffer of pH 7.0 and whose injection volume was 100 µl at a flow rate of 0.6 ml/min.

We claim:

1. Electrochemical enzyme biosensor which comprises noble metal electrodes and with which an electrochemical oxidation of pyridine necleotides takes place, characterized in that the noble metal electrodes have a microtexture rich in surface pores and have catalytic properties which reduce the overpotential required for electrochemical oxidation of the pyridinine necleotides.

2. Electrochemical enzyme biosensor according to claim 1, characterized in that, owing to the microtextures the surface area of the electrode is from 3 to 10 times larger than its geometric surface area.

3. Electrochemical enzyme biosensor according to claim 2, characterized in that the electrode surface comprises noble metal particles having a mean radius of curvature of from 0.05 µm to 4 µm.

4. The biosensor of claim 3 wherein the mean radius of curvature of the noble metal particles is from 0.5 to 2 µm.

5. The biosensor of claim 2 wherein the surface area is from 4 to 7 times larger than the geometric area.

6. Electrochemical enzyme biosensor according to claim 1, characterized in that the electrodes are made of gold.

7. Electrochemical enzyme biosensor according to claim 1, characterized in that the electrodes are coated with a membrane in which selectivity-determining biocomponents are immobilized.

8. Electrochemical enzyme biosensor according to claim 1, characterized in that enzymes or other biocomponents are immobilized directly on the electrodes via reactive pendent groups.

9. The biosensor of claim 1 wherein the pyridine nucleotide is NADH.

* * * * *